(12) United States Patent
Kietzmann

(10) Patent No.: US 10,449,299 B2
(45) Date of Patent: Oct. 22, 2019

(54) INJECTION DEVICE FOR DISPENSING A MEDICAMENT

(75) Inventor: Hardy Kietzmann, Berlin (DE)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 1313 days.

(21) Appl. No.: 12/576,374

(22) Filed: Oct. 9, 2009

(65) Prior Publication Data

US 2010/0152667 A1 Jun. 17, 2010

Related U.S. Application Data

(63) Continuation of application No. PCT/EP2008/002787, filed on Apr. 9, 2008.

(30) Foreign Application Priority Data

Apr. 18, 2007 (DE) .................. 10 2007 018 696

(51) Int. Cl.
*A61M 5/315* (2006.01)
*A61M 5/24* (2006.01)

(52) U.S. Cl.
CPC .... *A61M 5/31551* (2013.01); *A61M 5/31556* (2013.01); *A61M 5/31573* (2013.01);
(Continued)

(58) Field of Classification Search
CPC ........ A61M 5/31551; A61M 2205/583; A61M 2205/585; A61M 2005/3125;
(Continued)

(56) References Cited

U.S. PATENT DOCUMENTS 533,575 A 2/1895 Wilkens
3,973,554 A * 8/1976 Tipton ................ A61M 5/1785
250/506.1
(Continued)

FOREIGN PATENT DOCUMENTS

CA 2138528 C 12/1998
CA 2359375 * 7/2000
(Continued)

OTHER PUBLICATIONS

"Pen-injectors for medical use—Part 1: Pen-injectors—Requirements and test methods," International Standard, reference No. ISO 11608-1:2000(E), first edition Dec. 15, 2000, 32 pages.
(Continued)

*Primary Examiner* — Bhisma Mehta
*Assistant Examiner* — Laura C Schell
(74) *Attorney, Agent, or Firm* — Fish & Richardson P.C.

(57) ABSTRACT

Injection device for dispensing a medicament, comprising: a cartridge module, a dispensing mechanism which is actuated to dispense the injectable preparation, a dose-setting mechanism for setting the dose at which the injectable preparation is dispensed when the dispensing mechanism is actuated, the dose-setting mechanism comprising: a housing part (11) in which at least part of the dispensing mechanism is received, a display sleeve (13) rotatable therein, and an insertion sleeve (15) that can be inserted into the housing part (11), wherein
  the insertion sleeve (15) has, on its outer face, a raised surface section (20) that is transparent at least in some areas, and
  the housing part (11) has a recess (25) which is open at its distal edge (24) and which receives the insertion sleeve (15) in a rotationally fixed manner from the direction of the open end of the recess (25),
(Continued)

Figure 1:
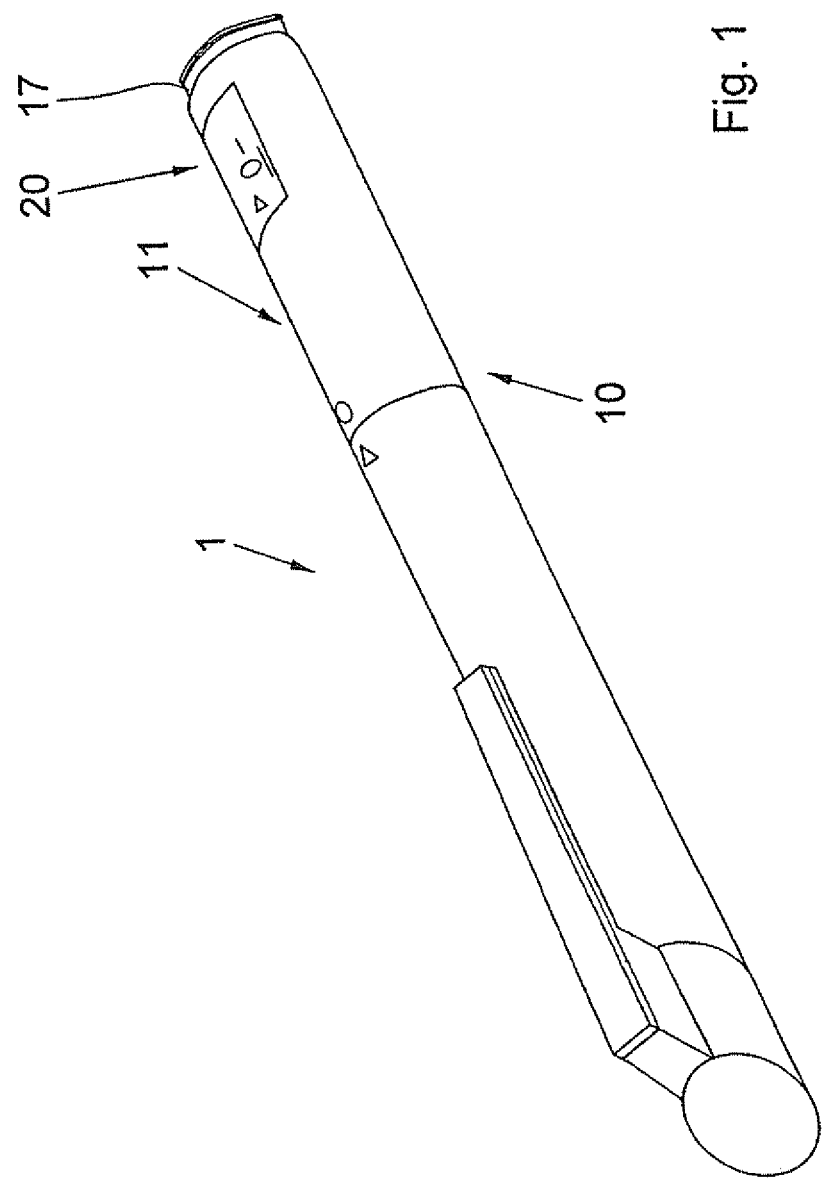

and insertion sleeve for an injection device, dose-setting mechanism for an injection device for dispensing a medicament, and method for assembling an injection device.

15 Claims, 11 Drawing Sheets

(52) U.S. Cl.
CPC ......... *A61M 5/24* (2013.01); *A61M 2205/583* (2013.01); *A61M 2205/585* (2013.01); *Y10T 29/49826* (2015.01)

(58) Field of Classification Search
CPC ........ A61M 2005/3126; A61M 5/1785; A61M 5/31533–31658; A61M 5/31573; A61M 2205/58
USPC .................................................. 604/210, 211
See application file for complete search history.

(56) References Cited

U.S. PATENT DOCUMENTS

| | | | |
|---|---|---|---|
| 4,865,591 A | 9/1989 | Sams | |
| 5,042,977 A | 8/1991 | Bechtold et al. | |
| 5,092,842 A | 3/1992 | Bechtold et al. | |
| 5,114,406 A | 5/1992 | Gabriel et al. | |
| 5,226,895 A | 7/1993 | Harris | |
| 5,226,896 A | 7/1993 | Harris | |
| 5,279,586 A | 1/1994 | Balkwill | |
| 5,304,152 A | 4/1994 | Sams | |
| 5,320,609 A | 6/1994 | Haber et al. | |
| 5,378,233 A | 1/1995 | Haber et al. | |
| 5,383,865 A | 1/1995 | Michel | |
| 5,391,157 A | 2/1995 | Harris et al. | |
| 5,480,387 A | 1/1996 | Gabriel et al. | |
| 5,505,704 A | 4/1996 | Pawelka et al. | |
| 5,582,598 A | 12/1996 | Chanoch | |
| 5,626,566 A | 5/1997 | Petersen et al. | |
| 5,674,204 A | 10/1997 | Chanoch | |
| 5,688,251 A | 11/1997 | Chanoch | |
| 5,807,346 A | 9/1998 | Frezza | |
| 5,820,602 A | 10/1998 | Kovelman et al. | |
| 5,851,079 A | 12/1998 | Horstman et al. | |
| 5,921,966 A | 7/1999 | Bendek et al. | |
| 5,957,896 A | 9/1999 | Bendek et al. | |
| 5,961,495 A | 10/1999 | Walters et al. | |
| 6,004,297 A | 12/1999 | Steenfeldt-Jensen et al. | |
| 6,193,698 B1 | 2/2001 | Kirchhofer et al. | |
| 6,221,046 B1 | 4/2001 | Burroughs et al. | |
| 6,221,053 B1 * | 4/2001 | Walters ............. | A61M 5/31551 604/208 |
| 6,235,004 B1 | 5/2001 | Steenfeldt-Jensen et al. | |
| 6,248,095 B1 | 6/2001 | Giambattista et al. | |
| 6,562,006 B1 | 5/2003 | Hjertman et al. | |
| 6,613,023 B2 | 9/2003 | Kirchhofer et al. | |
| 6,699,224 B2 | 3/2004 | Kirchhofer et al. | |
| 6,899,698 B2 | 5/2005 | Sams | |
| 6,932,794 B2 | 8/2005 | Giambattista et al. | |
| 6,936,032 B1 | 8/2005 | Bush, Jr. et al. | |
| 7,169,132 B2 | 1/2007 | Bendek et al. | |
| 7,241,278 B2 | 7/2007 | Moller | |
| 7,351,227 B2 * | 4/2008 | Lemer ................ | A61M 5/1785 604/192 |
| 7,678,084 B2 | 3/2010 | Judson et al. | |
| 7,850,662 B2 | 12/2010 | Veasey et al. | |
| 8,187,233 B2 | 5/2012 | Harms et al. | |
| 2002/0052578 A1 | 5/2002 | Moller | |
| 2002/0120235 A1 | 8/2002 | Enggaard | |
| 2003/0050609 A1 | 3/2003 | Sams | |
| 2004/0030292 A1 | 2/2004 | Gurtner | |
| 2004/0059299 A1 | 3/2004 | Moller | |
| 2004/0097883 A1 | 5/2004 | Roe | |
| 2004/0210199 A1 | 10/2004 | Atterbury et al. | |
| 2004/0267207 A1 | 12/2004 | Veasey et al. | |
| 2005/0113765 A1 | 5/2005 | Veasey et al. | |
| 2005/0177115 A1 | 8/2005 | Broennimann | |
| 2005/0197626 A1 | 9/2005 | Moberg et al. | |
| 2006/0153693 A1 | 7/2006 | Fiechter et al. | |
| 2007/0016143 A1 | 1/2007 | Miller et al. | |
| 2008/0269688 A1 * | 10/2008 | Colucci ............. | A61M 5/31551 604/189 |
| 2009/0275916 A1 | 11/2009 | Harms et al. | |

FOREIGN PATENT DOCUMENTS

| | | |
|---|---|---|
| CA | 2359375 A1 | 7/2000 |
| DE | 69521577 | 6/2002 |
| DE | 69910969 | 7/2004 |
| EP | 0496141 A1 | 7/1992 |
| EP | 0688571 | 12/1995 |
| EP | 0897729 A2 | 2/1999 |
| EP | 0937471 A2 | 8/1999 |
| EP | 0937476 A2 | 8/1999 |
| EP | 1557189 | 7/2005 |
| EP | 1642607 | 4/2006 |
| EP | 1776975 A2 | 4/2007 |
| WO | 93/07922 A1 | 4/1993 |
| WO | 93/24160 A1 | 12/1993 |
| WO | WO 99/03522 | 1/1999 |
| WO | 99/38554 A1 | 8/1999 |
| WO | WO 99/640952 | 12/1999 |
| WO | 01/10484 A1 | 2/2001 |
| WO | 02/030495 A2 | 4/2002 |
| WO | WO 02/064199 | 8/2002 |
| WO | 02/092153 A2 | 11/2002 |
| WO | 03/080160 A1 | 10/2003 |
| WO | WO 2006/037434 | 4/2006 |
| WO | 2006/084876 A1 | 8/2006 |

OTHER PUBLICATIONS

Written Opinion in Application No. PCT/EP2008/002787, dated Oct. 20, 2009, 7 pages (English Translation).

* cited by examiner

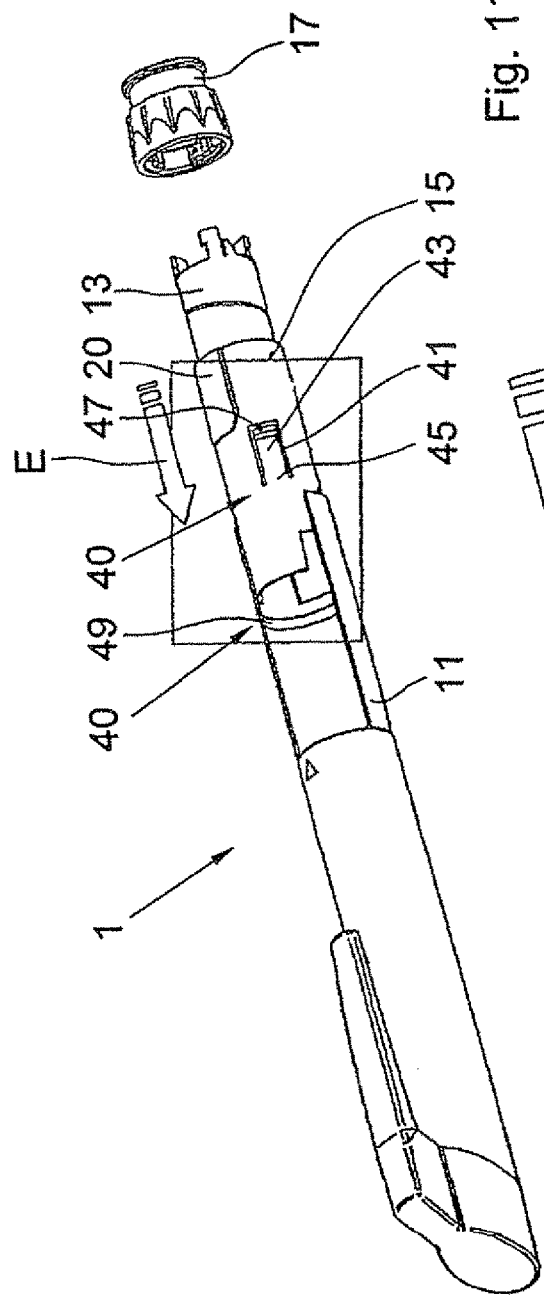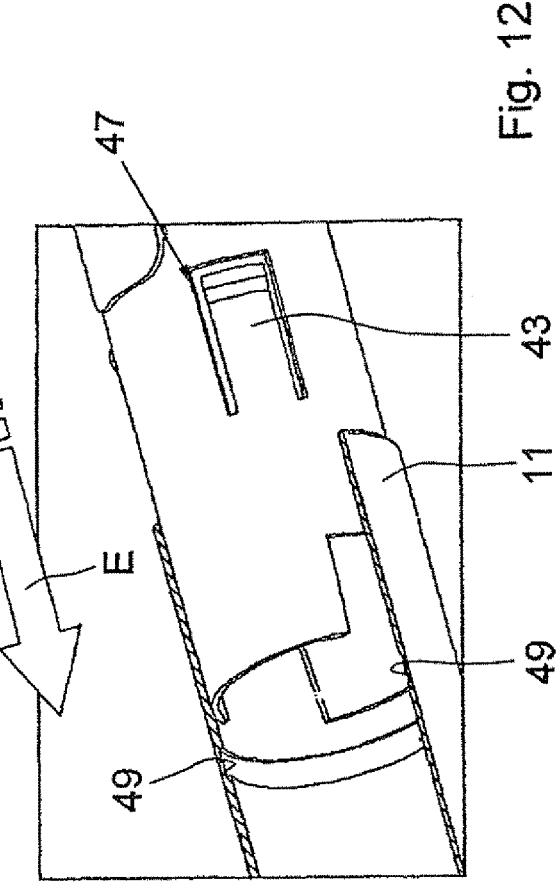

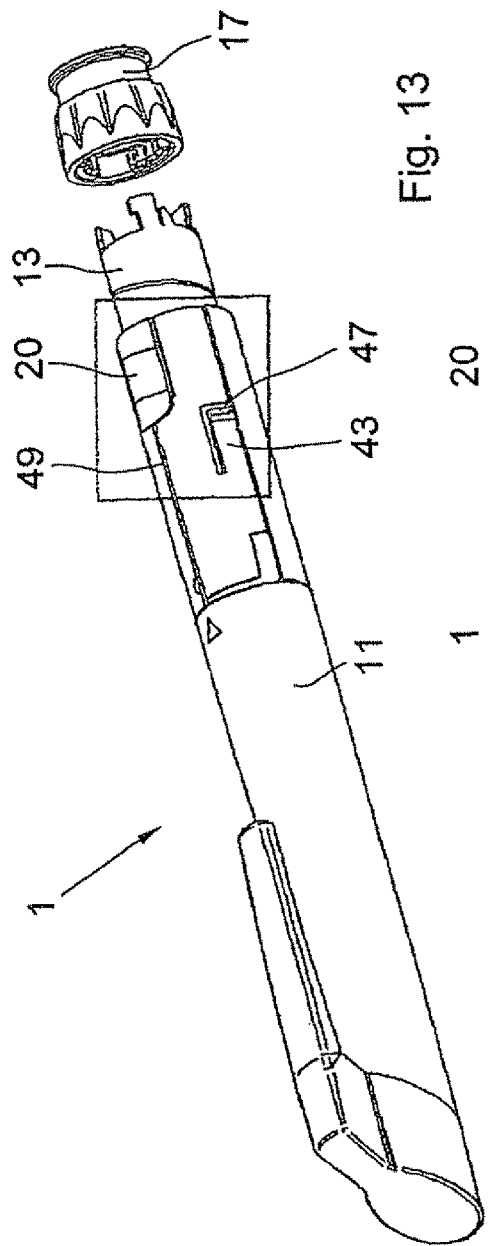
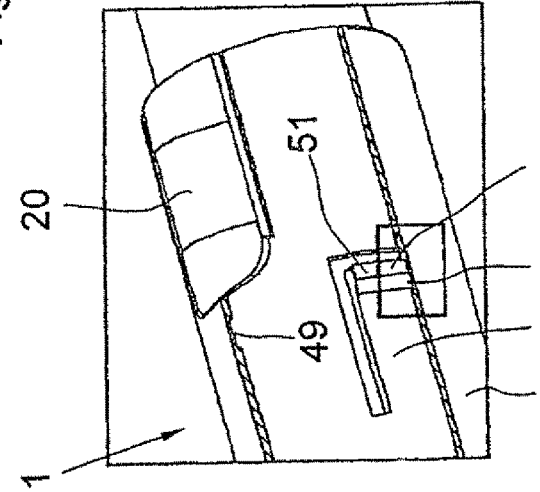
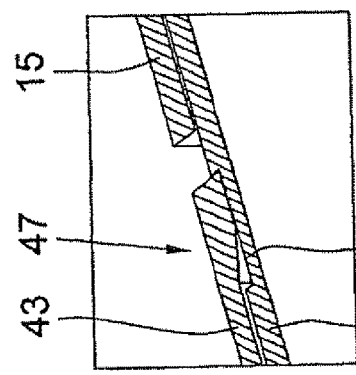
Fig. 13
Fig. 14
Fig. 15

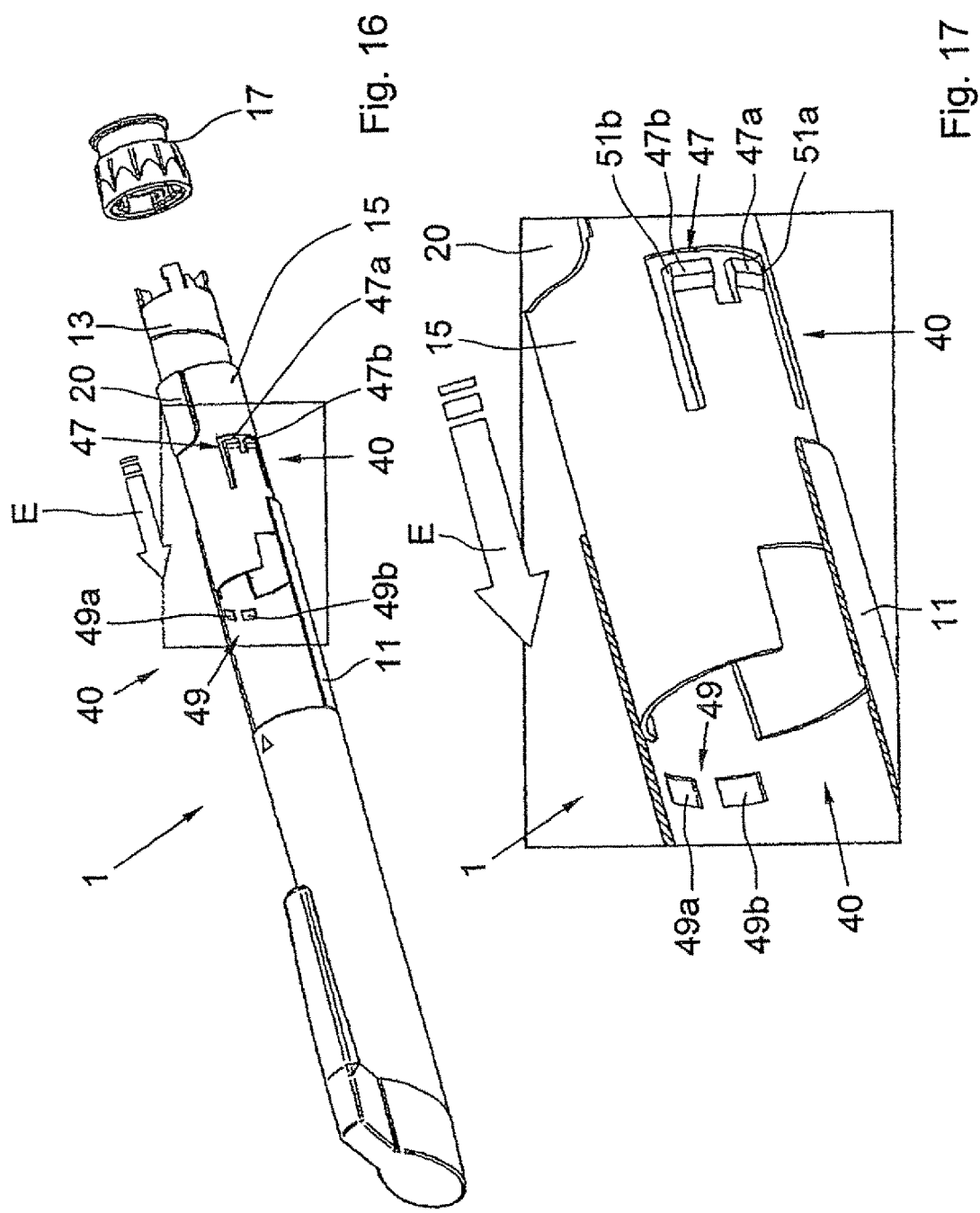

INJECTION DEVICE FOR DISPENSING A MEDICAMENT

The invention relates to an injection device for dispensing a medicament.

It is an object of the invention to make available an injection device with which it is possible to achieve an improved setting of the dose that is to be injected.

A further object of the invention is to make available a medical injection device with which the dosing accuracy for the user can be improved.

This object is achieved by the features of the independent claims. Further embodiments are set forth in the dependent claims referring back to these.

By means of the solution according to the invention, the dispensing mechanism and/or the dose-setting mechanism is mechanically strengthened and the set dose is easier to read off.

In one embodiment of the solution according to the invention, the interior of the housing of the injection device can be advantageously sealed off against contamination.

According to the invention, moreover, the insertion sleeve can be fitted into the distal housing part with an interference fit provided by suitable dimensioning of the raised section and of the recess, such that the axial position of the display sleeve can be more accurately set.

In this way, any manufacturing inaccuracies on structural parts of the injection device can be compensated.

The subject matter of the invention is therefore an injection device for dispensing a medicament, comprising:
 a cartridge module for receiving a cartridge containing an injectable preparation and if appropriate with a seat for attachment of a needle, which is mounted on one end of the cartridge and through which the injectable preparation can be injected,
 a dispensing mechanism which is actuated to dispense the injectable preparation,
 a dose-setting mechanism for setting the dose at which the injectable preparation is dispensed when the dispensing mechanism is actuated, the dose-setting mechanism comprising: a housing part in which at least part of the dispensing mechanism is received, a display sleeve, which can be fitted at least partially into the distal housing part and is rotatable therein, and an insertion sleeve that can be inserted into the housing part,
wherein
 the insertion sleeve has, on its outer face, a raised surface section that is transparent at least in some areas, and
 the housing part has a recess which is open at its distal edge and which receives the raised surface section from the direction of the open end of the recess, and the insertion sleeve in the inserted state is received in a rotationally fixed manner by the housing part.

In one embodiment of the invention, the mutually facing inner faces of the edges of the recess that extend in the axial direction of the distal housing part are spaced apart from each other by a distance at which the recess edges and the respective side edges of the raised surface section form a clearance fit, transition fit or interference fit.

In another embodiment of the invention, the contour lines of the abutting edge of the raised surface section and, accordingly, of the abutting edge of the recess extend rectilinearly and in the circumferential direction.

Preferably, the contour lines of the abutting edge of the raised surface section and, accordingly, of the abutting edge of the recess are formed by two line sections which extend at an angle to each other, and which in particular taper to a point, or the contour lines of the longitudinal edges and of the abutting edge of the raised surface section and, accordingly, of the longitudinal edges and of the abutting edge of the recess are formed as curve lines, such that the contours of the raised surface section and of the recess are at least partially oval in shape, or the contour lines of the longitudinal edges of the raised surface section and, accordingly, of the longitudinal edges of the recess extend rectilinearly and in particular parallel to each other, and the contour lines of the abutting edge of the raised surface section and, accordingly, of the abutting edge of the recess are formed as curve lines.

In another embodiment of the injection device according to the invention, the top of the raised surface section has a further projection formed thereon, in particular for achieving a magnifying glass effect in the transparent part of the raised surface section.

In yet another embodiment of the injection device according to the invention, a locking device is provided for locking the insertion sleeve to the housing part in the axial direction, when the insertion sleeve is pushed to its end position into the housing part, the locking device preferably having a receiving device, arranged on the inner face of the housing part, and an outwardly protruding sleeve engagement part which is arranged on the insertion sleeve and cooperates with the receiving device.

It is also preferable that the sleeve engagement part has a tongue, which extends in a recess of the housing part and which, at its proximal end, is connected to the insertion sleeve and, at its distal end, forms a free end with a locking projection.

In the injection device according to the invention, the receiving device can be designed as a depression on the inner face of the housing part or as a recess, and the receiving device preferably has a predetermined width in the circumferential direction or is designed as a circumferential depression on the inner circumference of the housing part.

In the injection device according to the invention, the free end can be designed as a singly or multiply divided free end in each case with a locking projection, and the receiving device can have one or more depressions or recesses.

In the injection device according to the invention, several tongues can be provided in the circumferential direction on the insertion sleeve, and several corresponding receiving devices can be arranged on the housing part.

Alternatively, in the injection device according to the invention, pairs of tongues and receiving devices can be arranged at the same axial position or can be offset from one another in the axial direction.

Moreover, in the injection device according to the invention, the housing part can be provided with a seal along at least part of the edge of the recess. In yet another embodiment of the injection device according to the invention, one or more seals are arranged on the distal end and/or on the inner face of the insertion sleeve.

Moreover, in the injection device according to the invention, several raised surface sections and, accordingly, several recesses on the insertion sleeve can be provided.

The raised surface section can be provided with one or more markings that make it easier to read off the dose that has been set and is indicated on the display sleeve, and the markings can be applied by physical or chemical means, in particular by printing or laminating.

In another embodiment of the injection device according to the invention, the longitudinal edges and/or the abutting edges of recess and raised surface section are designed such that they engage in each other with a form fit.

A further subject matter of the invention is an insertion sleeve for the injection device according to the invention, wherein the outer face of the insertion sleeve has a raised surface section for receiving the insertion sleeve in a recess of a housing part in a rotationally fixed manner, the surface section being transparent at least in some areas. Further particular embodiments of the insertion sleeve according to the invention can be derived from the above comments in connection with the description of the injection device according to the invention.

In another embodiment of the insertion sleeve according to the invention, the side edges of the raised surface section are configured in such a way that they form a clearance fit, transition fit or interference fit with inner faces of the edges of the recess of the housing part that extend in the axial direction of the distal housing part, and the contour line of the abutting edge of the raised surface section extends rectilinearly and in the circumferential direction, or the contour line of the abutting edge of the raised surface section is formed by two line sections which extend at an angle to each other, and which in particular taper to a point, or the contour lines of the longitudinal edges and of the abutting edge of projection are formed as curve lines, such that the contours of the raised surface section are at least partially oval in shape, or the contour lines of the longitudinal edges of the raised surface section extend rectilinearly and in particular parallel to each other, and the contour line of the abutting edge of the raised surface section is formed as a curve line.

In yet another embodiment of the insertion sleeve according to the invention, the top of the raised surface section has a further projection formed thereon, in particular for achieving a magnifying glass effect in the transparent part of the further projection.

In another embodiment, the insertion sleeve according to the invention comprises a part of a locking device for locking to a receiving device on the housing part in the end position of the insertion sleeve, where the part of the locking device arranged on the insertion sleeve preferably has an outwardly protruding sleeve engagement part which cooperates with the receiving device, and the sleeve engagement part also preferably having a tongue, which extends in a recess of the housing part and which, at its proximal end, is connected to the insertion sleeve and, at its distal end, forms a free end with a locking projection.

The free end can be designed as a singly or multiply divided free end in each case with a locking projection. Moreover, several tongues can be provided in the circumferential direction on the insertion sleeve, and they can be arranged at the same axial position or can be offset from one another in the axial direction.

Several raised surface sections can also be provided on the insertion sleeve according to the invention.

In another embodiment of the insertion sleeve according to the invention, the raised surface section is provided with one or more markings that make it easier to read off the dose that has been set and is indicated on a display sleeve extending through the insertion sleeve, said markings being applied by physical or chemical means, in particular by printing or laminating.

In yet another embodiment of the insertion sleeve according to the invention, the longitudinal edges and/or the abutting edges of the raised surface section are designed such that they engage in each other with a form fit with longitudinal edges and/or abutting edges of the recess of the housing part.

In yet another embodiment of the insertion sleeve according to the invention, one or more seals are arranged on the distal end and/or on the inner face of the insertion sleeve.

A further subject matter of the invention is a dose-setting mechanism for an injection device for dispensing a medicament, containing an insertion sleeve according to the invention.

Finally, a further subject matter of the invention is a method for assembling an injection device, wherein an insertion sleeve according to the invention is introduced into a housing part with a recess open at the distal edge.

Figure 2:
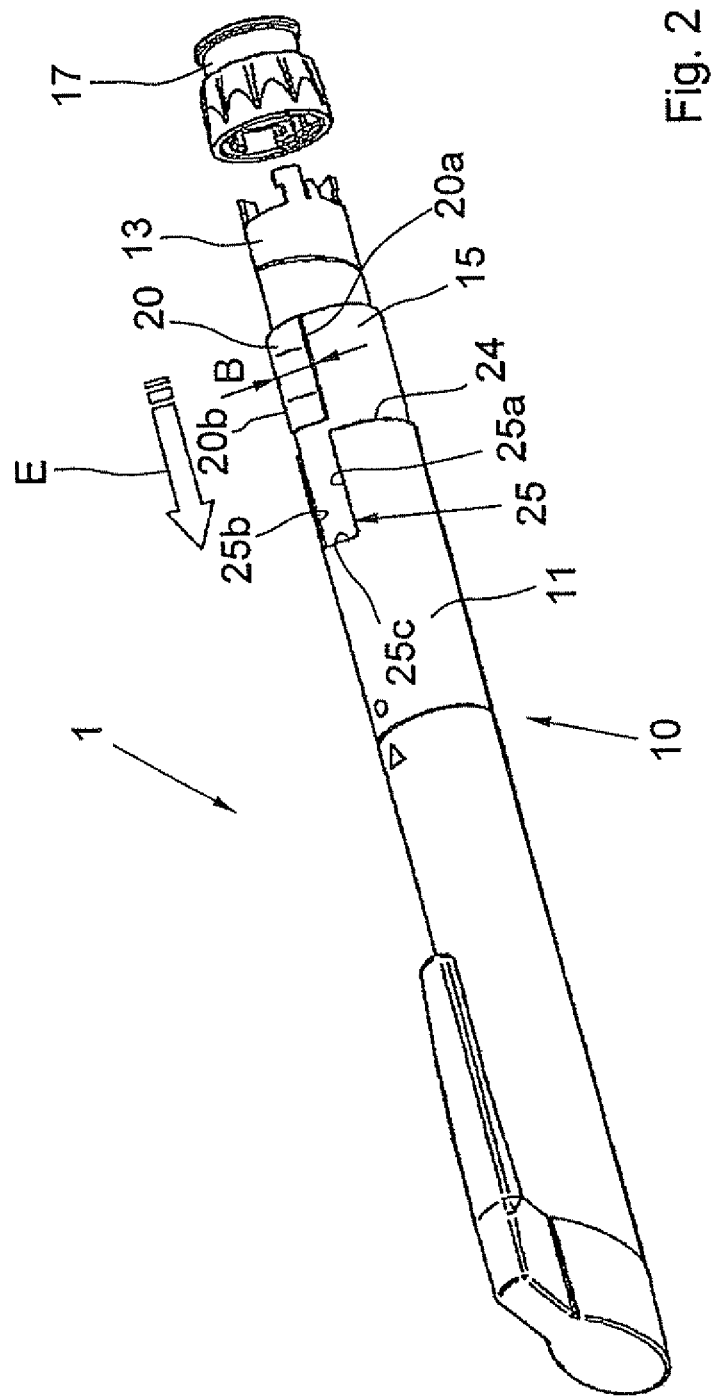
Figure 3:
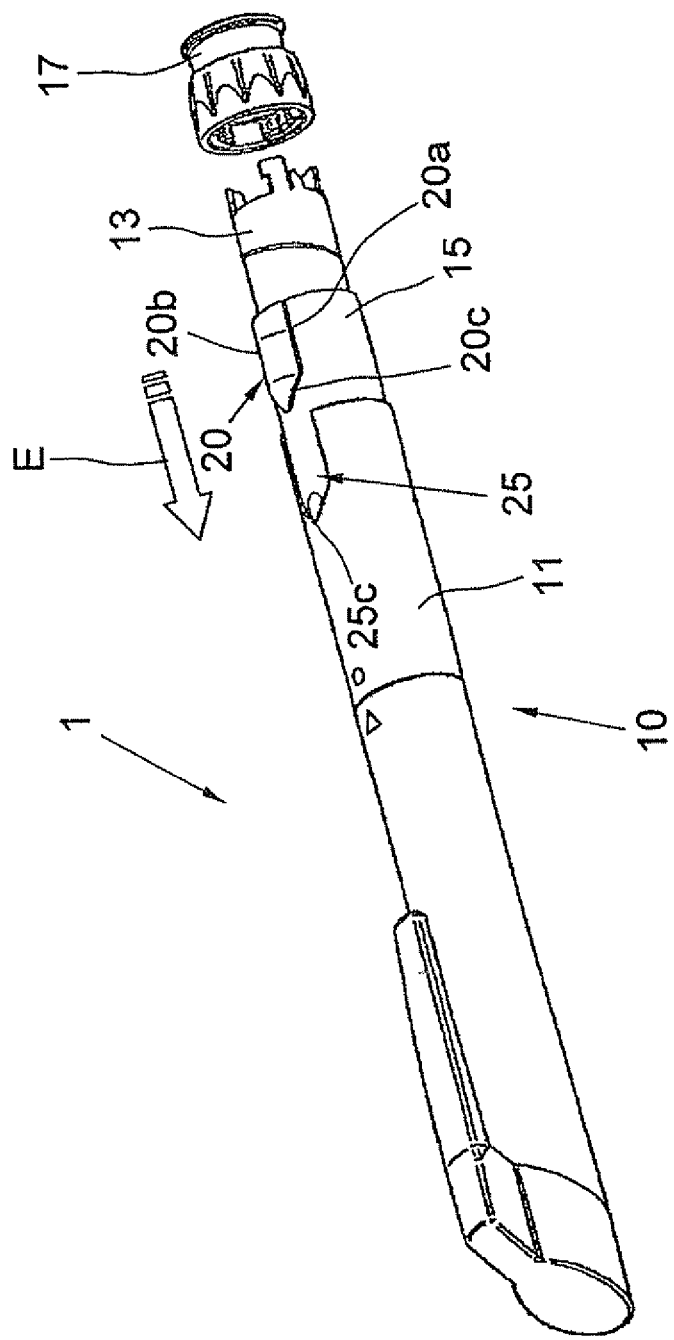
Figure 4:
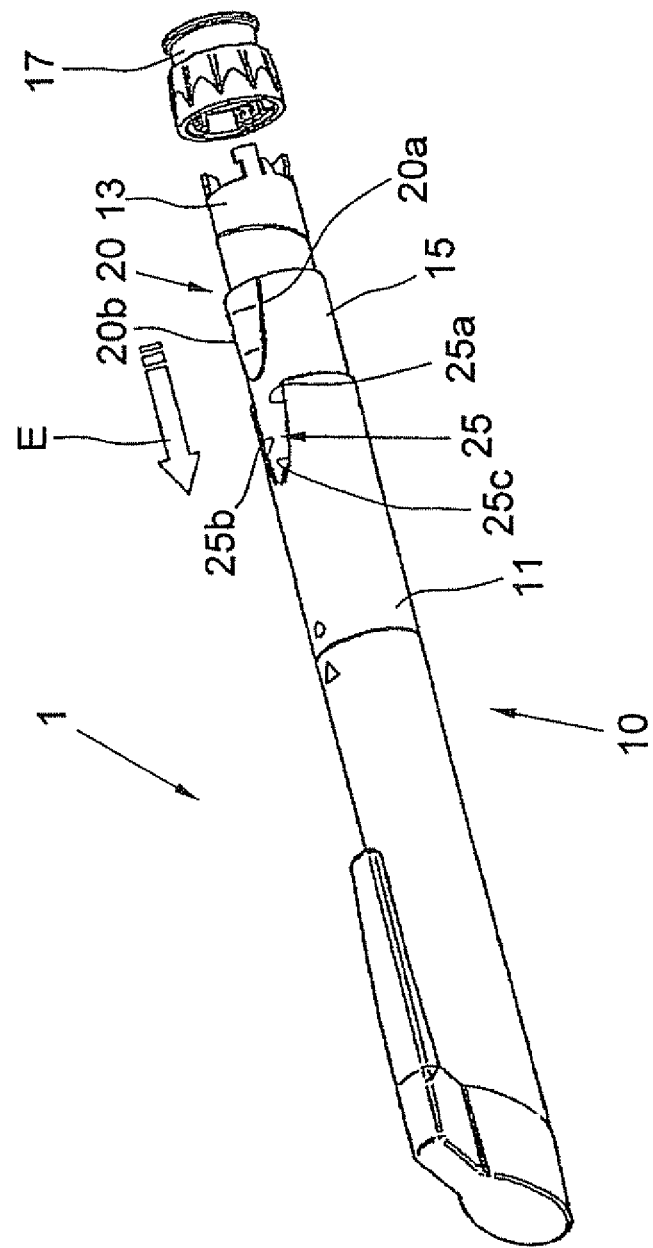
Figure 5:
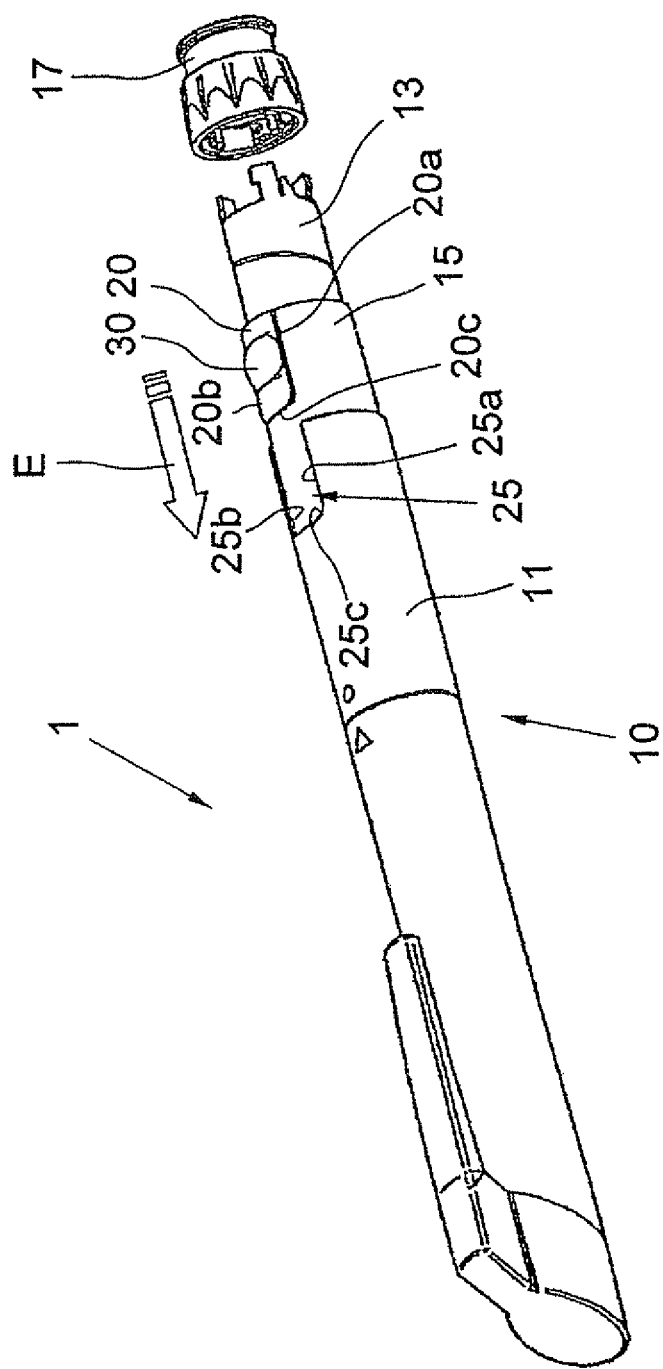
Figure 6:
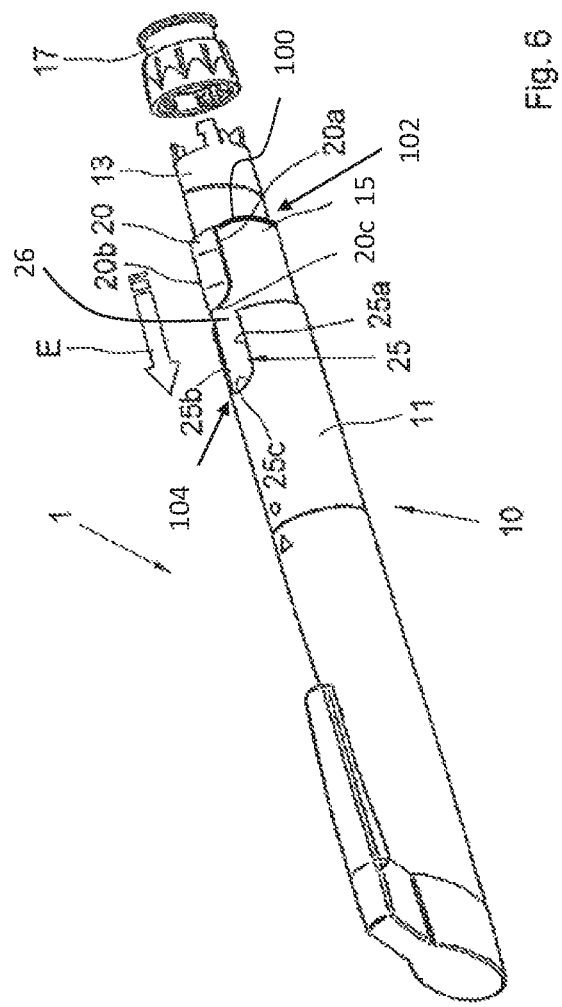
Figure 7:
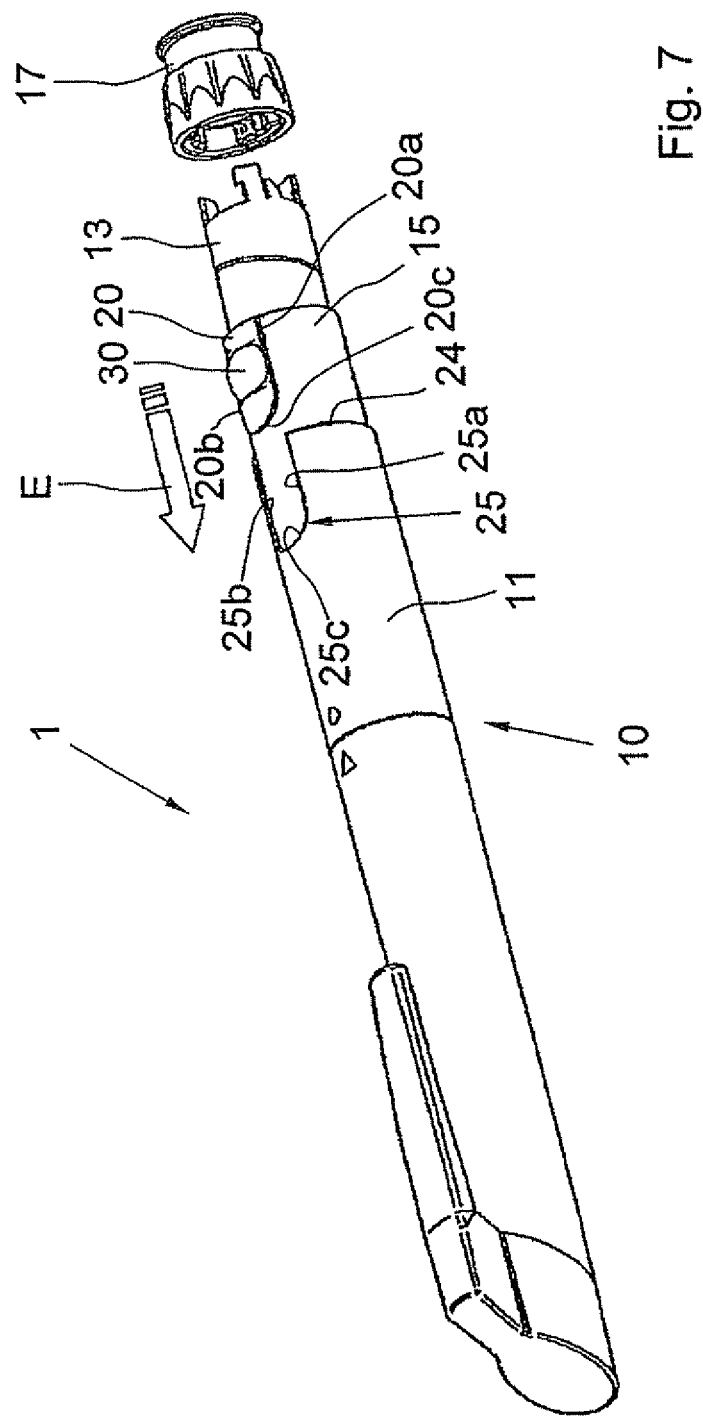
Figure 8:
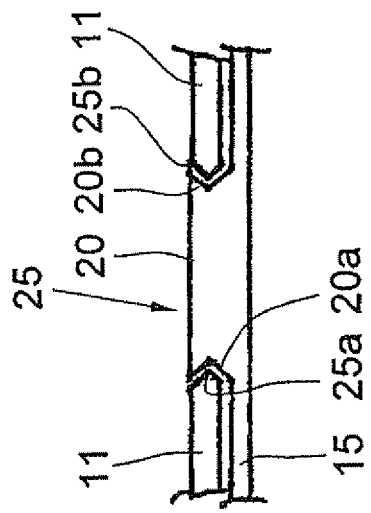
Figure 9:
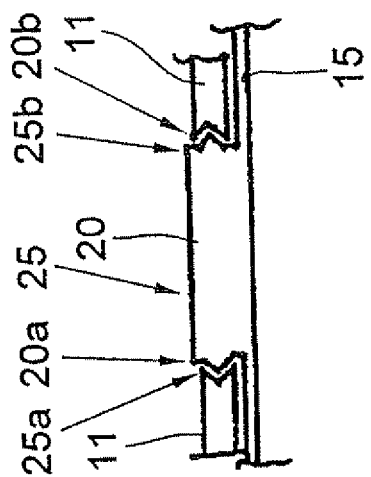
Figure 10:
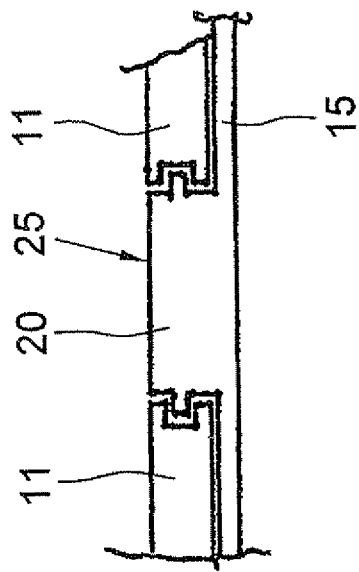

The invention is described below with reference to the figures, in which:

FIG. 1 shows a perspective view of a first embodiment of the injection device according to the invention, with a cap mounted on its front part, FIG. 2 shows a perspective schematic view of the first embodiment of the injection device according to the invention from FIG. 1, FIG. 3 shows a perspective schematic view of a second embodiment of the injection device according to the invention, FIG. 4 shows a perspective schematic view of a third embodiment of the injection device according to the invention, FIG. 5 shows a perspective schematic view of a fourth embodiment of the injection device according to the invention, FIG. 6 shows a perspective schematic view of a fifth embodiment of the injection device according to the invention, FIG. 7 shows a perspective schematic view of a sixth embodiment of the injection device according to the invention, FIG. 8 shows a view of the embodiment of the profiles of the edge lines of a recess and of a raised surface section of the injection device according to the invention, seen in transverse section, where the cylindrical shape of the components of the injection device and in particular of the housing and of the display sleeve are not taken into account, FIG. 9 shows a view, in accordance with the view in FIG. 8, of another embodiment of the profiles of the edge lines of the recess and of the raised surface section of the injection device according to the invention, seen in transverse section, FIG. 10 shows a view, in accordance with the view in FIG. 8, of another embodiment of the profiles of the edge lines of the recess and of the raised surface section of the injection device according to the invention, seen in transverse section, FIGS. 11 to 17 show different embodiments of a locking device for locking the insertion sleeve to the housing part in the axial direction.

To describe the invention, some of the terms used in the description and in the claims are explained below:

The terms "proximal" and "distal" are used to define the relative positions of components of the injection device according to the invention. Here, "proximal" means the end of the respective component directed toward the patient when the injection device is being used as intended, that is to say the end directed toward the injection needle. Accordingly, "distal" means the end of the respective component directed away from the "proximal" end.

The container mentioned hereinafter for receiving an injectable preparation can in particular be a cartridge or an ampule, it being possible for the container to be designed in different configurations, for example cylindrical or provided with other cross-sectional shapes.

The invention is based on injection devices for receiving and injecting medical injectable preparations (solution, suspension, emulsion) which are suitable for manual or automatic, mechanical or electromechanical administration and work according to the principle of displacement of the injectable preparation from a cartridge into an injection needle by means of a plunger guided axially in the cartridge. Such injection devices are either designed as disposable devices or as reusable devices.

The injection device according to the invention comprises:
a cartridge module preferably with a cartridge holder, with a cartridge for receiving the injectable preparation and if appropriate an injection needle that can be mounted thereon, which injection needle is mounted on one end of the cartridge or of the cartridge holder and through which the injectable preparation can be injected,
a dispensing mechanism or drive mechanism or force-transmitting mechanism whose actuation dispenses the injectable preparation, and
a dose-setting mechanism for setting the dose, which defines the amount of injectable preparation that is dispensed upon actuation of the dispensing mechanism.

The injection device 1 according to the invention for dispensing a medicament comprises, in one illustrative embodiment, a housing in which a container for receiving an injectable preparation is inserted. The housing can be composed of a front or proximal housing part and of a rear or distal housing part. Alternatively, the injection device according to the invention can be formed by a one-part or monobloc housing or by another housing configuration.

The cartridge or the container for receiving an injectable preparation comprises, for example: a proximal end and a distal end, a cylindrical or other longitudinal wall with an inner face and an outer face, a front opening for delivery of the injectable preparation, and a rear opening into which a plunger movable along the inner face can be guided. In its starting position, i.e. with the container completely filled, the plunger is preferably located at the distal end of the container. The container can be fitted directly into the housing with an opening at its proximal end or, if appropriate, into a front housing part for insertion into the housing.

If the injection device is designed as a reusable device, the container is duly replaced after it has been emptied.

Thus, the container for receiving an injectable preparation can be fitted into a container-receiving device or a container housing or a container holder with a proximal end and a distal end. Alternatively, however, the container holder can also serve as an outer housing. In this case, the front housing part serves as part of the outer housing for receiving the container. An injection needle (not shown) can be mounted or is fixed on the proximal end of the container, which injection needle extends if appropriate through an opening at the proximal end of the outer housing or of the container housing and/or through an opening at the proximal end of the housing into the container.

The injection device according to the invention for dispensing a medicament thus comprises in particular: a housing for insertion of the container that holds an injectable preparation, and the container with a front proximal end which is provided with a front opening provided for delivery of the injectable preparation, for insertion into a proximal end of the housing, and with a rear end which is provided with a rear opening and on which there is fitted, in its starting position, a plunger displaceable in the axial direction of the cartridge by means of the dispensing device.

The dose-setting element is formed by:
a housing part 11 which, in a two-part design of the housing, is preferably the distal housing part, in which at least part of the dispensing mechanism is received,
a display sleeve 13, which can be fitted at least partially into the distal housing part and is rotatable therein, and
an insertion sleeve 15 that can be inserted into the distal housing part, and, in the fitted state, is received in a rotationally fixed manner, preferably in a rotationally and axially fixed manner, by the housing 10.

For this purpose, the internal diameter of the insertion sleeve 15 and the external diameter of the display sleeve 13 are provided such that the display sleeve 13 can be guided into the insertion sleeve 15.

The dispensing mechanism is coupled to the dose-setting mechanism. The dose-setting mechanism cooperates mechanically with the dispensing mechanism. The dose-setting mechanism can be an integral component part of the dispensing mechanism or can be a component part separate from the dispensing mechanism.

The dispensing mechanism effects the dispensing of the injectable preparation, the dose of the dispensed injectable preparation being set by means of the dose-setting mechanism. To dispense or administer the injectable preparation, the dispensing mechanism can have an actuating element 17, for example in the form of an injection button, and a plunger coupled directly or indirectly to the injection button by means of a plunger rod.

The dose-setting mechanism thus has a dose-setting function in which the dose is set in particular by setting the axial position of the display sleeve 13 relative to the distal housing part upon uncoupling of the display sleeve 13 from the plunger.

The insertion sleeve can have an inner thread into which a corresponding mating threaded piece of the display sleeve can be received, such that the display sleeve moves axially upon rotation relative to the insertion sleeve, in order to define, via a set axial position, the dose of injectable preparation to be dispensed.

If appropriate, the insertion sleeve can be connected to other parts of the injection device, for example to the cartridge module, and can in particular be engaged with these parts or locked onto these parts.

The injection device has a dose-administering function in which the dose of injectable preparation defined by means of the dose-setting mechanism is dispensed by actuation of an actuating device coupled to the plunger. For this purpose, the plunger rod of the dispensing mechanism is guided for example axially inside the housing or the distal housing part, such that an axial movement of the plunger rod causes an axial movement of the plunger in the proximal direction, which leads to dispensing of the injectable preparation. The actuating device is actuated by the person using the injection device and in particular by a patient or by medical personnel or by a control means, in order to effect the dispensing of the injectable preparation. The actuating and dosing device converts the actuating movement of the actuating element into a defined axial movement of the plunger rod, which in turn effects a defined movement of the plunger, in order to dispense a defined amount of the injectable preparation through the injection needle when actuated by the patient.

The insertion sleeve has a cylindrical main body, defined between a terminal distal end 102 and a terminal proximal end 104, that can be guided into the distal housing part. For the distal housing part to receive the insertion sleeve 15 in a rotationally fixed manner, the insertion sleeve 15 further comprises on its outer face a stepped or raised surface section or projection 20, that entirely protrudes outward from a single circumferential portion of the outer face of the cylindrical main body, and which is transparent at least in some areas.

In another embodiment of the invention, the raised surface section 20 is provided with one or more markings (arrows, lines or the like) which are able to make it easier to read off, through the insertion sleeve, the dose that has been set and is indicated on the display sleeve. These markings can be applied, for example, by printing or laminating, by mechanical or chemical means such as printing, laminating, cutting, etching or the like.

The housing has a recess 25, which is open at its distal edge and which has a shape such that, when the insertion sleeve 15 is inserted into the distal housing part 11 in the direction of insertion E, the stepped or raised surface section 20 is guided into the recess from the direction of the open edge 26 of the recess.

The shape of the stepped or raised surface section 20 is provided in such a way that the surface section fits with predetermined precision in the circumferential direction into the recess, i.e. the mutually facing inner faces of the edges 25a, 25b of the recess 25 that extend in the axial direction of the distal housing part are spaced apart by a distance a certain extent greater or smaller than the width B of the stepped or raised surface section 20 in the circumferential direction of the insertion sleeve. Alternatively, the corresponding recess edges 25a, 25b and the stepped or raised surface section 20 can form a clearance fit, a transition fit or an interference fit.

The dimensioning of recess and of raised surface section 20 to provide a fit and the provision of the recess with an open edge 26 is advantageous in terms of assembly of the injection device, in particular since this can be done more easily and/or with greater precision, which can result, for example, in better automation of the assembly operation.

The recess 25 has an abutting edge or proximal edge which forms an abutment for the axial end position 20c of the raised surface section 20 or of the connecting edge 25c in the recess 25.

In one embodiment of the insertion sleeve, its inner face is provided with a guide device which cooperates with an optionally present outer thread of the display sleeve, in order to axially adjust the display sleeve as a function of the rotation position of the display sleeve 13. By means of a transition fit or interference fit, the axial position of the display sleeve 13 relative to the housing part 11 can be provided more precisely as a function of the respective rotation position of the display sleeve 13. In this way, it is possible in turn to increase the precision with which a set dose is dispensed by the injection device.

Moreover, by increasing the thickness of the raised surface section 20, for example by configuring it as a magnifying glass, the visibility of the dose setting can be increased. In this way, it is possible to improve the precision with which a set dose is dispensed by the user.

The shape of the stepped or raised surface section 20, with its axially extending side edges 20a, 20b and with its proximal edge or abutting edge 20c, and the shape of the recess 25 can be different:

As is shown in FIGS. 1 and 2, the abutting edge 20c of the raised surface section and, accordingly, the abutting edge 25c of the recess can extend rectilinearly and in the circumferential direction.

As is shown in FIG. 3, the abutting edge 20c of the raised surface section 20 and, accordingly, the abutting edge 25c of the recess can be formed by two line sections which extend at an angle to each other, and which in particular taper to a point.

As is shown in FIG. 4, the longitudinal edges 20a, 20b and the abutting edge 20c of the raised surface section 20 and, accordingly, the longitudinal edges 25a, 25b and the abutting edge 25c of the recess can be formed as a curve line, such that the contours of the raised surface section 20 and the recess are partially oval in shape.

As is shown in FIG. 5, it is possible, in each alternative configuration of the contours of the raised surface section 20, for the top of the latter to have a further projection 30 formed on it, in particular in order to provide a magnifying glass effect in the transparent part of the further projection 30.

As is shown in FIG. 6, the longitudinal edges 20a, 20b of the raised surface section 20 and, accordingly, the longitudinal edges 25a, 25b of the recess 25 can extend rectilinearly and in particular parallel to each other, and the abutting edge 20c of the raised surface section 20 and, accordingly, the abutting edge 25c of the recess 25 can be formed as a curve line.

As is shown in FIG. 7, it is possible, particularly in the configuration of the contours of the raised surface section 20 according to FIG. 6, for the top thereof to have a further projection 30 formed thereon, in particular in order to provide a magnifying glass effect in the transparent part of the further projection 30.

According to the invention, a locking device can also be provided for locking the insertion sleeve 15 to the housing part 11 in the axial direction. This can be done in different ways. For example, the outer face, i.e. the face of the insertion sleeve 15 directed towards the housing part 11, can be provided with a locking projection, and a corresponding point on the inner face of the housing part 11 can be provided with a locking groove or a locking depression or a locking recess in particular in the form of a locking aperture, which lock with one another when the insertion sleeve 15 is pushed to its end position into the housing part 11.

The edges of the recess and of the raised section can be configured in different ways. For example, the longitudinal edges and/or the abutting edges of recess 25 and raised section 20 can be configured such that they engage with a form fit. The respective edge faces of recess 25 and raised surface section 20 can form a dovetail guide or other type of guide. FIGS. 8 to 10 show configurations of the edge faces for the longitudinal edges of the raised surface section and of the recess, although these can alternatively or additionally be formed on the edge faces of the abutting edges.

FIG. 8 shows a dovetail guide in which the edge face of the longitudinal edge 20a, 20b of the raised surface section has an angled guide part that engages in a correspondingly angled recess in the edge face of the recess 25. FIG. 9 shows a variant of the dovetail guide according to FIG. 8, where the edge face of the recess 25 conversely has an angled guide part that engages in a corresponding angled recess in the longitudinal edge 20a, 20b of the raised surface section 20. In the embodiment of the guide according to FIG. 10, the guide in the edge face of the recess is designed as a groove, while the edge face of the raised surface section has a corresponding mating piece that engages in the groove. Analogously, the groove can also be formed alternatively in the edge face of the recess and the corresponding mating piece can be formed in the edge face of the raised surface section.

Along the recess edge, the distal housing part can be provided with a seal in order to more effectively seal the interior of the distal housing part from contamination and/or moisture.

A seal can be arranged along the edges of the recess 25, that is to say along the longitudinal edges 25a, 25b and the abutting edge. Alternatively or in addition, a seal 100 can be arranged at the distal end and on the inner face of the insertion sleeve 15 and preferably along the edge of the distal end of the insertion sleeve 15. This seal is preferably designed as a seal extending around the outer circumference of the insertion sleeve 15. The seal can have an annular shape and in particular brush shape. In the aforementioned alternatives, the seal can in particular extend around the opening of the distal edge of the insertion sleeve 15.

The aforementioned seal on the insertion sleeve 15 acts between the inner face of the insertion sleeve 15 and the outer face of the display sleeve 13 and serves in particular to reduce or prevent the entry of particles or of liquid between the display sleeve 13 and the insertion sleeve 15 and thus to reduce or prevent contamination of the interior of the housing part 11.

To prevent contamination of the interior of the housing part 11, a seal can alternatively or additionally be arranged on the distal end and on the outer face of the insertion sleeve 15 and preferably along the edge of the distal end of the insertion sleeve 15. In addition, or alternatively, such a seal can also extend on the proximal face of the raised surface section 20 about the circumference of the outer face of the insertion sleeve 15.

It is also possible to provide several stepped or raised surface sections 20 and, correspondingly, several recesses 25 on the injection device 1.

FIGS. 11 to 17 show different embodiments of the locking device 40 for locking the insertion sleeve 15 to the housing part 11 in the axial direction.

The locking device 40 can have a receiving device 49 and also a tab or tongue 43 which extends in a depression or a recess 41 of the housing part 11 and which, at its proximal end 45, is connected to the insertion sleeve 15 and, at its distal end, forms a free end 47. The free end 47 forms an outwardly protruding edge area 51, 51a, 51b in the form of a locking projection, which engages in a receiving device 49 when the insertion sleeve 15 is pushed to its end position into the housing part 11. The locking projection 51, 51a, 51b can be formed by an outwardly extending and angled extension of the tongue 43 and/or by a locking cam 51, 51a, 51b formed at the free end 47.

As is shown in FIGS. 11 to 15, the receiving device 49 cooperating with the locking device 40 can be designed as a depression on the inner face of the housing part 11. Alternatively, the receiving device 49 can be designed as a recess in the form of an aperture (FIGS. 16 and 17).

In the circumferential direction, the receiving device 49 can extend by a width that corresponds to the width of the locking projection 51, 51a, 51b and/or creates a fit with which the insertion sleeve forms a fit. Such a fit is preferably provided instead of the aforementioned fit designed with the projection. The receiving device 49 can extend in the circumferential direction beyond the width of the locking projection 51, 51a, 51b and in particular can be designed as a depression on the inner circumferential face of the housing part 11 (FIGS. 11 and 12).

The free end 47 can be designed as a singly or multiply divided free end, such that one or more locking projections 51, 51a, 51b and in particular one or more locking cams can be provided. FIGS. 16 and 17 show an embodiment of the locking device with a singly divided free end and thus with two locking projections 51a, 51b in the form of locking cams. Accordingly, the receiving device 49 has two depressions or recesses 49a, 49b.

Several tongues 43 can be provided in the circumferential direction and, accordingly, several receiving devices such as depressions or recesses.

In the embodiments with several pairs of tongues 43 and receiving devices, these can be arranged at the same axial position or can be mutually offset in the axial direction.

What is claimed is:

1. An insertion sleeve for an injection device, the insertion sleeve having a cylindrical main body defined between a terminal distal end and a terminal proximal end, and comprising an outer face that is cylindrical and positioned between the terminal distal end and the terminal proximal end,
    wherein a distal end portion of the outer face has a raised surface section that entirely protrudes radially outward from a single circumferential portion of the outer face of the cylindrical main body,
    wherein the raised surface section of the insertion sleeve has a proximal abutting edge and longitudinally and axially extending side edges and is configured to be received in a recess located at a distal end of a housing part such that the insertion sleeve cannot rotate relative to the housing part,
    wherein the distal end of the housing part has an inner face,
    wherein the distal end of the housing part and the distal end portion of the outer face are directed away from a needle of the injection device,
    wherein the raised surface section of the insertion sleeve has at least one transparent area,
    wherein the outer face of the insertion sleeve has a locking device that is configured to engage a receiving device located on the inner face of the housing part to lock the insertion sleeve to the housing part in a longitudinal axial direction,
    wherein the distal end of the housing part and the inner face of the housing part are a unitary structure defining an outermost housing of the injection device,
    wherein the longitudinally and axially extending side edges of the raised surface section are configured in such a way that they form a clearance fit, transition fit or interference fit with inner faces of edges of the recess that extend in the longitudinal axial direction, and
    wherein the insertion sleeve comprises an inner thread.

2. The insertion sleeve as claimed in claim 1, wherein a contour line of the proximal abutting edge of the raised surface section extends rectilinearly and in a circumferential direction.

3. The insertion sleeve as claimed in claim 1, wherein a contour line of the proximal abutting edge of the raised surface section is formed by two line sections which extend at an angle to each other, and which in particular taper to a point.

4. The insertion sleeve as claimed in claim 1, wherein contour lines of the longitudinally and axially extending side edges and of the proximal abutting edge of the raised surface section are formed as curve lines, such that the contour lines of the raised surface section are at least partially oval in shape.

5. The insertion sleeve as claimed in claim 1, wherein contour lines of the longitudinally and axially extending side edges of the raised surface section extend rectilinearly and parallel to each other, and a contour line of the proximal abutting edge of the raised surface section is formed as a curve line.

6. The insertion sleeve as claimed in claim 1, wherein the at least one transparent area of the raised surface section has a projection formed thereon for achieving a magnifying glass effect.

7. The insertion sleeve as claimed in claim 1, wherein part of the locking device arranged on the insertion sleeve has an outwardly protruding sleeve engagement part which cooperates with the receiving device.

8. The insertion sleeve as claimed in claim 1, wherein the locking device comprises a tongue, wherein a proximal end of the tongue is connected to the insertion sleeve and a distal end of the tongue forms a free end with a locking projection which extends into another recess of the housing part.

9. The insertion sleeve as claimed in claim 8, wherein the free end is designed as a singly or multiply divided free end.

10. The insertion sleeve as claimed in claim 8, wherein several tongues are provided in a circumferential direction on the insertion sleeve.

11. The insertion sleeve as claimed in claim 10, wherein several of the several tongues are arranged at a same axial position or are offset from one another in an axial direction.

12. The insertion sleeve as claimed in claim 1, wherein the raised surface section is provided with one or more markings that make it easier to read off a dose that has been set and is indicated on a display sleeve extending through the insertion sleeve.

13. The insertion sleeve as claimed in claim 12, wherein the one or more markings are applied by physical or chemical means, the physical or chemical means comprising printing or laminating.

14. The insertion sleeve as claimed in claim 1, wherein a seal is arranged on a distal end and/or on an inner face of the insertion sleeve.

15. The insertion sleeve as claimed in claim 1, wherein the recess is configured to receive the raised surface section from a distal direction.

* * * * *